(12) United States Patent
Johnson et al.

(10) Patent No.: US 8,796,225 B2
(45) Date of Patent: *Aug. 5, 2014

(54) REGULATION OF IMMUNE RESPONSES BY MODULATION OF THE FUNCTION OF ANTIGEN PRESENTING CELLS

(75) Inventors: Barbara Jane Johnson, Roadvale (AU); Caroline Amanda Dobbin, Holland Park (AU); Inge E A Flesch, Holt (AU)

(73) Assignee: CBIO Limited, Eight Mile Plains (AU)

( * ) Notice: Subject to any disclaimer, the term of this patent is extended or adjusted under 35 U.S.C. 154(b) by 1235 days.

This patent is subject to a terminal disclaimer.

(21) Appl. No.: 12/281,291

(22) PCT Filed: Mar. 1, 2007

(86) PCT No.: PCT/AU2007/000254
§ 371 (c)(1),
(2), (4) Date: Feb. 8, 2010

(87) PCT Pub. No.: WO2007/098557
PCT Pub. Date: Sep. 7, 2007

(65) Prior Publication Data
US 2010/0256059 A1    Oct. 7, 2010

(30) Foreign Application Priority Data
Mar. 2, 2006   (AU) ................ 2006901058

(51) Int. Cl.
*A61K 38/16* (2006.01)
*A61K 38/17* (2006.01)

(52) U.S. Cl.
USPC ............... 514/21.2; 514/17.9; 514/1.7

(58) Field of Classification Search
None
See application file for complete search history.

(56) References Cited

FOREIGN PATENT DOCUMENTS

| WO | WO 02/40038 A2 | 5/2002 |
|---|---|---|
| WO | WO 2007/006095 A2 | 5/2002 |
| WO | WO 2004/041300 A1 | 5/2004 |
| WO | WO 2005/067959 A1 | 7/2005 |

OTHER PUBLICATIONS

Dobbin, C., et al., "Heat Shock Protein 10 Modulates Innate Immunity Through Interaction with Multiple Toll-like Receptor Family Members," *Tissue Antigens*, vol. 66(5), 248, pp. 433-434 (2005).

Johnson, B., et al., "Heat Shock Protein 10 Inhibits Lipopolysaccharide-induced Inflammatory Mediator Production," *The Journal of Biological Chemistry*, vol. 280(6), pp. 4037-4047 (2005).

Chua-Intra, B., et al., "T-Cell Recognition of Mycobacterial GroES Peptides in Thai Leprosy Patients and Contacts" *Infection and Immunity*, vol. 66(10), pp. 4903-4909 (1998).

*Primary Examiner* — Elizabeth C Kemmerer
(74) *Attorney, Agent, or Firm* — Ditthavong & Steiner, P.C.

(57) ABSTRACT

The present invention relates to the use of chaperonin 10 to modulate the function of antigen presenting cells. More particularly the invention resides in the modulation of cell surface expression of MHC molecules such as HLA.

20 Claims, 4 Drawing Sheets

REGULATION OF IMMUNE RESPONSES BY MODULATION OF THE FUNCTION OF ANTIGEN PRESENTING CELLS

CROSS-REFERENCE TO RELATED APPLICATIONS

This application is a U.S. National Stage Application of PCT/AU2007/000254 filed Mar. 1, 2007, which claims priority to Australian Provisional Application No. 2006901058 filed Mar. 2, 2006, the contents of which are hereby incorporated by reference in their entirety.

FIELD OF THE INVENTION

The present invention relates generally to the regulation of immune responses by modulation of the function of antigen-presenting cells (APCs). In particular, the present invention relates to the use of chaperonin 10 in the modulation of APC function such as cell surface expression of major histocompatibility complex (MHC) molecules, for example, HLA, and to associated methods, uses and compositions for the treatment of diseases, and to processes for screening modulators of APC function.

BACKGROUND OF THE INVENTION

A central component of host defence systems against invading bacterial and viral pathogens involves the successful recognition of the pathogen, or components thereof, by cellular receptors which induce a signalling cascade resulting in stimulation of the immune system. An essential aspect of this system is T-cell recognition of major histocompatibility complex-(MHC)-peptide complexes.

$CD4^+$ T-cells are able to recognize pathogen-derived peptides when such peptides are displayed in the context of MHC class II molecules, which are composed of an $\alpha$- and $\beta$-chain originally assembled in the endoplasmic reticulum. These $\alpha$- and $\beta$-chains associate with the invariant chain (Ii) which protects the peptide binding groove and facilitates trafficking of MHC class II molecules to endosomal compartments. In the endosomal compartments, Ii is cleared, leaving a peptide (CLIP) in the binding groove. The chaperone molecule HLA-DM facilitates replacement of CLIP by antigenic peptides. Mature MHC class II molecules loaded with antigenic peptide then migrate to the cell surface where they can be presented to $CD4^+$ T-cells.

This system of antigen processing and the presentation of mature MHC class II molecules occurs in dendritic cells (DC), which are the only APC that can stimulate naïve T cells and induce a primary immune response. Thus, DC play a pivotal role in antigen-presentation and the induction of adaptive immunity. The capacity of DC to induce an immune response is dependent on their maturation state. It is thought that immature DC expressing low levels of MHC and T cell co-stimulatory molecules such as CD40, CD80, CD83 and CD86 on the cell surface capture antigens in the periphery. They then migrate to secondary lymphoid tissues and undergo a maturation process. Upon maturation, MHC molecules are redistributed from intracellular compartments to the cell surface which results in an increased capacity to present antigens. Concomitantly, the surface expression of co-stimulatory molecules which promote T cell activation is up-regulated. The cytokine profile secreted by DC is also dependent on their maturation stage. Cytokines produced by mature DC include IL-12, IL-1$\alpha$/$\beta$, IL-18, IFN-$\alpha$/$\beta$, IL-6, TNF-$\alpha$, IL-10, and TGF-$\beta$. The DC cytokine profile finally determines the Th1/Th2-outcome of the immune response. That is, antigens that induce IL-12 secretion by DC induce Th1 differentiation while antigens that do not induce IL-12 production promote Th2 differentiation.

Many of the regulatory processes involved in DC maturation remain unknown. In particular, many of the molecular signalling pathways that are involved when MHC class II molecules undergo changes in localization from endosomal structures in immature DC to the plasma membrane in mature DC remain unclear.

Chaperonin 10 (Cpn10) is a highly conserved mitochondrial chaperone playing an essential role in protein folding. Cpn10 has also been shown to be involved in a number of immunomodulatory activities, for example, inhibition of nuclear factor-$\kappa$B (NF-$\kappa$B) activation and production of pro-inflammatory cytokines, both in vitro and in vivo. The present invention is predicated on the surprising and unexpected finding that Cpn10 has the capacity to modulate APC function, including redistribution of MHC molecules from intracellular compartments to the cell surface in DC, and APC-mediated activation of T cells.

SUMMARY OF THE INVENTION

According to a first aspect of the present invention, there is provided a method for modulating an immune response in a subject or in at least one cell, tissue or organ thereof, by modulating the level of cell surface expression of at least one MHC molecule, wherein said method comprises administering an effective amount of chaperonin 10.

The method may further comprise modulating an immune response in a subject or in at least one cell, tissue or organ thereof, by modulating the level of cell surface expression of at least one other cell surface molecule, comprising administering an effective amount of chaperonin 10.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The chaperonin 10 may be a naturally-derived, recombinantly produced or synthetically produced chaperonin 10. The chaperonin 10 may be of eukaryotic origin. The chaperonin 10 may be of mammalian origin. The chaperonin 10 may be human chaperonin 10.

The chaperonin 10 may comprise the polypeptide sequence as set forth in SEQ ID NO:1, SEQ ID NO:2 or SEQ ID NO:3. The chaperonin 10 may be acetylated or non-acetylated.

The chaperonin 10 may be administered in the form of a polynucleotide encoding chaperonin 10. The polynucleotide encoding chaperonin 10 may be located in a genetic construct, operably linked to a promoter. The polynucleotide may comprise the sequence as set forth in SEQ ID NO:4.

According to a second aspect of the present invention, there is provided a method for treating or preventing a disease or condition in a subject by modulating the level of cell surface expression of at least one MHC molecule, wherein said method comprises administering to the subject an effective amount of chaperonin 10.

The method may further comprise treating or preventing a disease or condition in a subject by modulating the level of cell surface expression of at least one other cell surface molecule, comprising administering an effective amount of chaperonin 10.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The disease or condition may result from, or be otherwise associated with, infection of the subject by a viral or bacterial pathogen. The disease or condition may be cancer, an autoimmune disorder, inflammation, allergy, asthma or infectious disease.

The chaperonin 10 may be a naturally-derived, recombinantly produced or synthetically produced chaperonin 10. The chaperonin 10 may be of eukaryotic origin. The chaperonin 10 may be human chaperonin 10.

The chaperonin 10 may comprise the polypeptide sequence as set forth in SEQ ID NO:1, SEQ ID NO:2 or SEQ ID NO:3. The chaperonin 10 may be acetylated or non-acetylated.

The chaperonin 10 may be administered in the form of a polynucleotide encoding chaperonin 10. The polynucleotide encoding chaperonin 10 may be located in a genetic construct, operably linked to a promoter. The polynucleotide may comprise the sequence as set forth in SEQ ID NO:4.

According to a third aspect of the present invention, there is provided a method for modulating the level of cell surface expression of at least one MHC molecule in a subject, or in at least one cell, tissue or organ thereof, wherein said method comprises administering an effective amount of chaperonin 10.

The method may further comprise modulating the level of cell surface expression of at least one other cell surface molecule in a subject, or in at least one cell, tissue or organ thereof, comprising administering an effective amount of chaperonin 10.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

According to a fourth aspect of the present invention, there is provided a method for modulating the function of an antigen-presenting cell in a subject, or in at least one tissue or organ thereof, wherein said method comprises administering an effective amount of chaperonin 10.

The antigen-presenting cell may be selected from the group comprising a macrophage, dendritic cell or B cell.

The function may be selected from the group comprising migration to a lymph node, T cell activation or T cell proliferation.

According to a fifth aspect of the present invention, there is provided a composition when used for the treatment or prevention of a disease or condition, wherein said composition comprises chaperonin 10 together with at least one pharmaceutically acceptable carrier, diluent or adjuvant, and wherein the chaperonin 10 modulates the level of cell surface expression of at least one MHC molecule.

The chaperonin 10 may further modulate the level of cell surface expression of at least one other cell surface molecule.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

According to a sixth aspect of the present invention, there is provided a composition when used for the treatment or prevention of a disease or condition, wherein said composition comprises chaperonin 10 together with at least one pharmaceutically acceptable carrier, diluent or adjuvant, and wherein the chaperonin 10 modulates the function of an antigen-presenting cell in a subject, or in at least one tissue or organ thereof.

The antigen-presenting cell may be selected from the group comprising a macrophage, dendritic cell or B cell.

The function may be selected from the group comprising migration to a lymph node, T cell activation or T cell proliferation.

According to a seventh aspect of the present invention, there is provided the use of chaperonin 10 for the manufacture of a medicament for the treatment or prevention of a disease or condition, wherein the chaperonin 10 modulates the level of cell surface expression of at least one MHC molecule.

The chaperonin 10 may further modulate the level of cell surface expression of at least one other cell surface molecule.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

According to an eighth aspect of the present invention, there is provided the use of chaperonin 10 for the manufacture of a medicament for the treatment or prevention of a disease or condition, wherein the chaperonin 10 modulates the function of an antigen-presenting cell in a subject, or in at least one tissue or organ thereof.

The antigen-presenting cell may be selected from the group comprising a macrophage, dendritic cell or B cell.

The function may be selected from the group comprising migration to a lymph node, T cell activation or T cell proliferation.

According to a ninth aspect of the present invention, there is provided a method for modulating the production, localization within a cell and/or cell surface expression of one or more immunomodulators in a subject, or at least one cell, tissue or organ thereof, wherein said method comprises administering an effective amount of chaperonin 10, and wherein the chaperonin 10 modulates the level of cell surface expression of at least one MHC molecule or at least one other cell surface molecule.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

According to a tenth aspect of the present invention, there is provided a process for identifying a compound that modulates an immune response, wherein said process comprises:

(a) contacting a cell or cell extract with a candidate compound in the presence of Cpn10; and (b) determining whether expression on the surface of said cell of at least one MHC molecule is modulated upon contact with said candidate compound.

The process may further comprise:

(c) determining whether expression on the surface of said cell of at least one other cell surface molecule is modulated upon contact with said candidate compound.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

According to an eleventh aspect of the present invention, there is provided a process for screening a plurality of compounds to identify a compound that modulates an immune response, wherein said process comprises:

(a) contacting a cell or cell extract with said plurality of compounds in the presence of Cpn10; and (b) determining whether expression on the surface of said cell of at least one MHC molecule is modulated upon contact with said plurality of compounds.

The process may further comprise:

(c) determining whether expression on the surface of said cell of at least one other cell surface molecule is modulated upon contact with said plurality of compounds.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

According to a twelfth aspect of the present invention, there is provided a process for inducing modulation of the level of cell surface expression of at least one MHC molecule in a subject, or in at least one cell, tissue or organ thereof, wherein said process comprises administering an effective amount of chaperonin 10.

The process may further comprise modulation of the level of cell surface expression of at least one other cell surface molecule in a subject, or in at least one cell, tissue or organ thereof, comprising administering an effective amount of chaperonin 10.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

According to a thirteenth aspect of the present invention, there is provided a process for identifying a compound that modulates an immune response, wherein said process comprises:

(a) contacting a cell or cell extract with a candidate compound in the presence of Cpn10; and (b) determining whether the migration of said cell to a lymph node or the ability to activate and/or cause proliferation of T cells is modulated upon contact with said candidate compound.

The cell may be an antigen-presenting cell. The antigen-presenting cell may be selected from the group comprising a macrophage, dendritic cell or B cell.

According to a fourteenth aspect of the present invention, there is provided a process for screening a plurality of compounds to identify a compound that modulates an immune response, wherein said process comprises:

(a) contacting a cell or cell extract with said plurality of compounds in the presence of Cpn10; and (b) determining whether the migration of said cell to a lymph node or the ability to activate and/or cause proliferation of T cells is modulated upon contact with said plurality of compounds.

The cell may be an antigen-presenting cell. The antigen-presenting cell may be selected from the group comprising a macrophage, dendritic cell or B cell.

According to a fifteenth aspect of the present invention, there is provided a process for modulating the function of an antigen-presenting cell in a subject, or in at least one tissue or organ thereof, wherein said process comprises administering an effective amount of chaperonin 10.

The antigen-presenting cell may be selected from the group comprising a macrophage, dendritic cell or B cell.

The function may be selected from the group comprising migration to a lymph node or T cell activation.

DEFINITIONS

In the context of this specification, the term "comprising" means "including principally, but not necessarily solely". Furthermore, variations of the word "comprising", such as "comprise" and "comprises", have correspondingly varied meanings.

As used herein the terms "treatment", "treating" and variations thereof, refer to any and all uses which remedy a disease state or symptoms, prevent the establishment of disease, or otherwise prevent, hinder, retard, or reverse the progression of disease or other undesirable symptoms in any way whatsoever.

As used herein the term "effective amount" includes within its meaning a non-toxic but sufficient amount of an agent or compound to provide the desired therapeutic or prophylactic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

The term "polypeptide" means a polymer made up of amino acids linked together by peptide bonds. The terms "polypeptide" and "protein" are used interchangeably herein, although for the purposes of the present invention a "polypeptide" may constitute a portion of a full length protein.

The term "polynucleotide" as used herein refers to a single- or double-stranded polymer of deoxyribonucleotide, ribonucleotide bases or known analogues or natural nucleotides, or mixtures thereof.

As used herein the terms "modulating", "modulates" and variations thereof refer to increasing or decreasing the level of activity, production, secretion or functioning of a molecule in the presence of a particular modulatory molecule or agent of the invention compared to the level of activity, production, secretion or other functioning thereof in the absence of the modulatory molecule or agent. These terms do not imply quantification of the increase or decrease. The modulation may be of any magnitude sufficient to produce the desired result and may be direct or indirect.

The term "immunomodulator" as used herein refers to a molecular mediator that plays a role in the activation, maintenance, maturation, inhibition, suppression or augmentation of an immune response.

The term "MHC molecule" refers to any molecule complexed to, associated with or forming a part of a major histocompatibility complex. An "MHC molecule" may therefore include a human leukocyte antigen (HLA) of any description, for example, including but not limited to HLA-DR (MHC class II), MHC class I molecules, or non-classical MHC molecules such as, for example, CD1a, CD1b or CD1c.

The term "other cell surface molecule" refers to any molecule expressed on the surface of a cell, and may or may not include a co-stimulatory molecule. The term "co-stimulatory molecule" refers to any molecule capable of contributing to, directly or indirectly, the transduction of signalling involving an MHC molecule.

BRIEF DESCRIPTION OF THE DRAWINGS

The present invention will now be described, by way of non-limiting example only, with reference to the accompanying drawings.

Human DCs were differentiated from monocytes in the presence of GM-CSF and IL-4 for 5 days. Conversion of monocytes into DC with LPS was verified by flow-cytometric analysis of CD1a and CD14 cell surface expression. CD1a$^+$ CD14$^-$ DC were further analysed for cell surface expression of the maturation marker HLA-DR. Cultured monocyte-derived DC were used to assess the capacity of Cpn10 to modulate LPS-induced DC maturation. The expression of HLA-DR was unchanged on immature DC incubated with Cpn10 (A). However, LPS-induced up-regulation of HLA-DR expression was significantly reduced by Cpn10 (A vs. B, p=0.0408; A vs. C, p=0.0324; A vs. D, p=0.0161) (B). Representative of 3 independent experiments.

Figure 2:
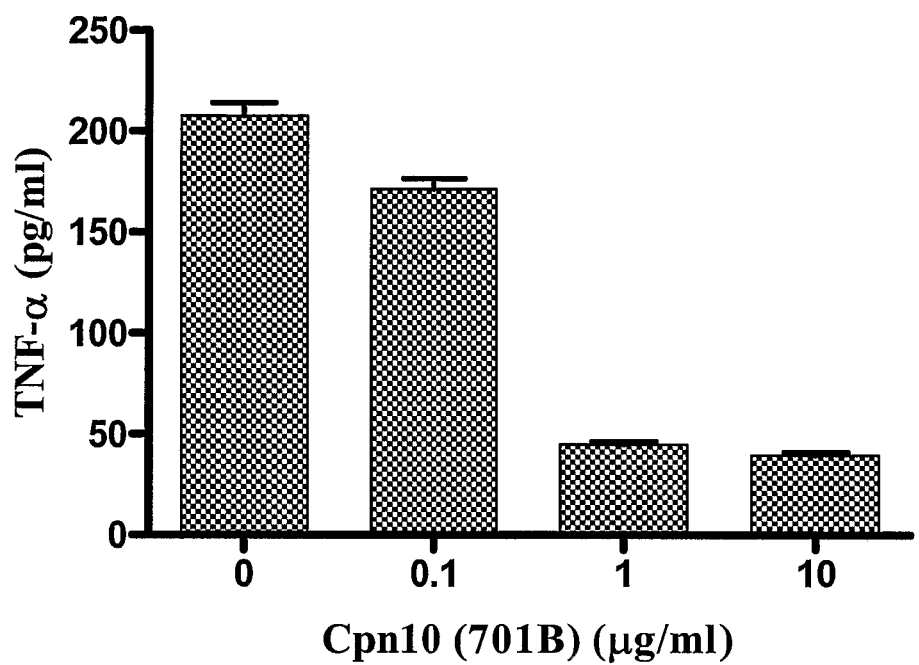

FIG. 2. Cpn10 diminishes constitutive TNF-α release by DC

Cultured monocyte-derived DC were used to assess the capacity of Cpn10 to modulate constitutive TNF-α release. DC were incubated with a concentration range of Cpn10 for 20 hours. TNF-α accumulation in culture supernatants was measured by ELISA. Data shown are representative of 4 independent experiments.

Figure 3:
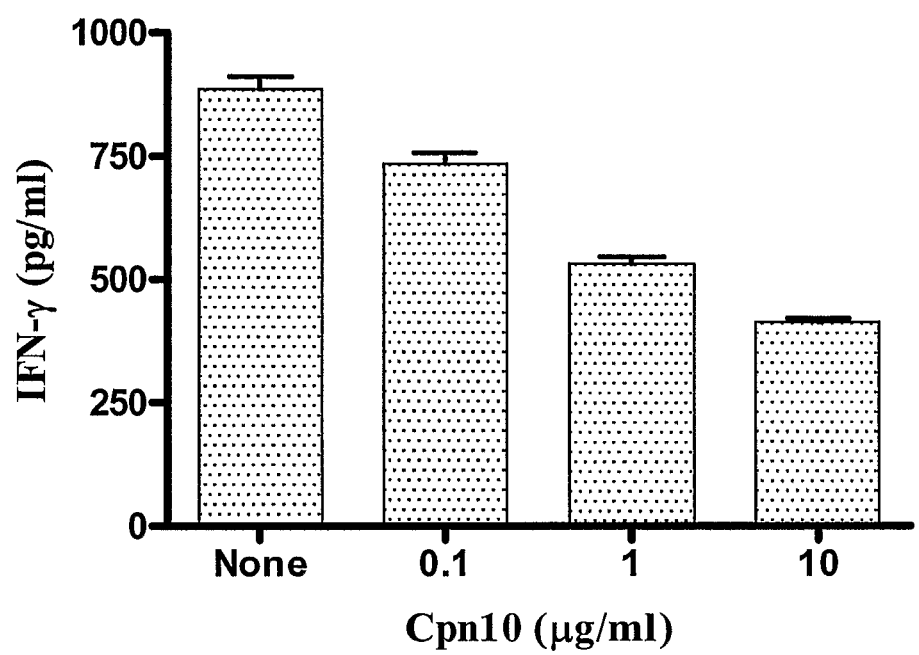

FIG. 3. Cpn10 reduces IFN-γ production in a primary mixed-leukocyte reaction (MLR)

Cultured monocyte-derived DC were used to assess the capacity of Cpn10 to modulate T cell activation by DC in a primary mixed-leukocyte reaction (MLR). DC were co-cultured with allogeneic CD$^+$ T cells for 6 days and IFN-γ production was measured in the culture supernatants by ELISA. IFN-γ accumulation was significantly reduced by Cpn10. Data are representative of 2 independent experiments.

Figure 4:
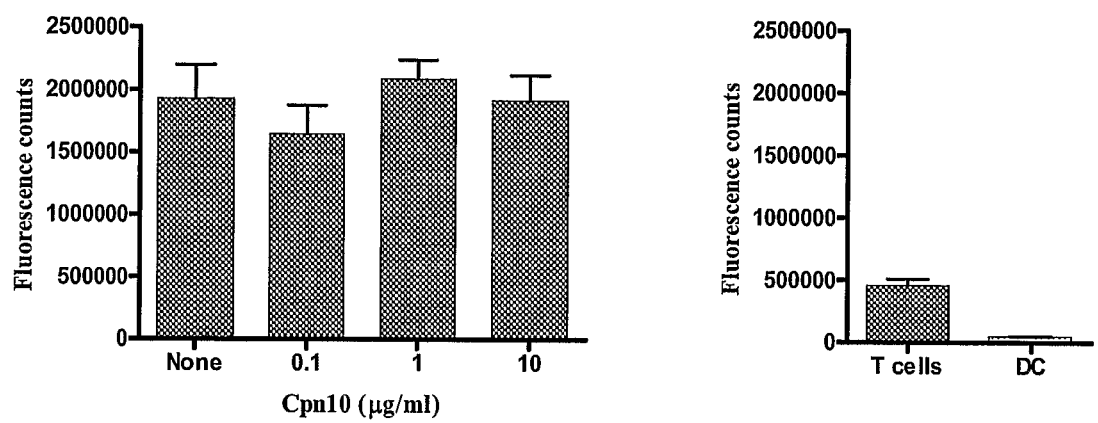

FIG. 4. Cpn10 does not affect T cell proliferation in a primary mixed-leukocyte reaction (MLR)

Cultured monocyte-derived DC and isolated allogeneic CD4$^+$ T cells were co-cultured in the presence or absence of Cpn10 for 6 days. Proliferation was measured using a CyQUANT cell proliferation assay kit according to the manufacturer's instructions. Representative of 2 independent experiments.

BEST MODE OF PERFORMING THE INVENTION

Using a fluorochrome labelled protein, the inventors have shown that Cpn10 interacts strongly with antigen presenting cells, primarily dendritic cells. Data from in vitro experiments, in which either myeloid or plasmacytoid dendritic cells (DC) from PBMC were specifically depleted prior to stimulating with a range of TLR ligands, showed appreciably changed dynamics of cytokine production in the presence of Cpn10. Moreover, the inventors demonstrated that monocyte-derived DC matured together with Cpn10 redistributed a reduced level of HLA-DR and other co-stimulatory molecules from intracellular compartments to the cell surface. This down-modulation of MHC class II molecule expression and reduced antigen-presenting capacity may contribute to the overall anti-inflammatory effects of Cpn10.

In particular, to assess the effect of Cpn10 on DC maturation, the inventors used monocyte-derived DC which have been characterized extensively in the past (J. Exp. Med. 1994; 179: 1109; Blood 2002; 99: 993; PNAS 1996; 93: 2588; Int. Immunol. 2004; 16: 767). Immature monocyte-derived DC are CD14$^-$ HLA-DR$^+$ CD1a$^+$ cells. Upon activation with LPS, they up-regulate HLA-DR and express stimulatory ligands for T cells on the cell surface. Here it is shown that Cpn10 modulates the extent of DC maturation in vitro.

The inventors have therefore shown that Cpn10 down-regulates LPS-induced expression of HLA-DR at the cell surface. This reduced HLA-DR expression may be consequent to reduced IFN-γ production by maturing DC (described in J. Immunol 1989; 143:3781). On the other hand, Cpn10-induced down-regulation of HLA-DR may reflect a change in the efficiency of the endocytic pathway to transport antigen-loaded MHC class II molecules to the cell surface. However, data presented herein provide clear evidence that the prevention of DC maturation and a reduced antigen-presenting capacity of DC and B cells are a likely mode of action of Cpn10 in amelioration of autoimmune disease.

Accordingly, the present invention provides methods for modulating an immune response in a subject or in at least one cell, tissue or organ thereof, by modulating the level of cell surface expression of at least one MHC molecule, wherein said methods comprise administering an effective amount of chaperonin 10.

The methods may further comprise modulating an immune response in a subject or in at least one cell, tissue or organ thereof, by modulating the level of cell surface expression of at least one other cell surface molecule, comprising administering an effective amount of chaperonin 10.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The chaperonin 10 may be a naturally-derived, recombinantly produced or synthetically produced chaperonin 10. The chaperonin 10 may be of eukaryotic origin. The chaperonin 10 may be of mammalian origin. The chaperonin 10 may be human chaperonin 10.

The chaperonin 10 may comprise the polypeptide sequence as set forth in SEQ ID NO:1, SEQ ID NO:2 or SEQ ID NO:3. The chaperonin 10 may be acetylated or non-acetylated.

The chaperonin 10 may be administered in the form of a polynucleotide encoding chaperonin 10. The polynucleotide encoding chaperonin 10 may be located in a genetic construct, operably linked to a promoter. The polynucleotide may comprise the sequence as set forth in SEQ ID NO:4.

The present invention also provides methods for treating or preventing a disease or condition in a subject by modulating the level of cell surface expression of at least one MHC molecule, wherein said methods comprise administering to the subject an effective amount of chaperonin 10.

The methods may further comprise treating or preventing a disease or condition in a subject by modulating the level of cell surface expression of at least one other cell surface molecule, comprising administering an effective amount of chaperonin 10.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The disease or condition may result from, or be otherwise associated with, infection of the subject by a viral or bacterial pathogen. The disease or condition may be cancer, an autoimmune disorder, inflammation, allergy, asthma or infectious disease.

The chaperonin 10 may be a naturally-derived, recombinantly produced or synthetically produced chaperonin 10. The chaperonin 10 may be of eukaryotic origin. The chaperonin 10 may be human chaperonin 10.

The chaperonin 10 may comprise the polypeptide sequence as set forth in SEQ ID NO:1, SEQ ID NO:2 or SEQ ID NO:3. The chaperonin 10 may be acetylated or non-acetylated.

The chaperonin 10 may be administered in the form of a polynucleotide encoding chaperonin 10. The polynucleotide encoding chaperonin 10 may be located in a genetic construct, operably linked to a promoter. The polynucleotide may comprise the sequence as set forth in SEQ ID NO:4.

The present invention additionally provides methods for modulating the level of cell surface expression of at least one MHC molecule in a subject, or in at least one cell, tissue or organ thereof, wherein said methods comprise administering an effective amount of chaperonin 10.

The methods may further comprise modulating the level of cell surface expression of at least one other cell surface molecule in a subject, or in at least one cell, tissue or organ thereof, comprising administering an effective amount of chaperonin 10.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The present invention further provides methods for modulating the function of an antigen-presenting cell in a subject, or in at least one tissue or organ thereof, wherein said methods comprise administering an effective amount of chaperonin 10.

The antigen-presenting cell may be selected from the group comprising a macrophage, dendritic cell or B cell.

The function may be selected from the group comprising migration to a lymph node, T cell activation or T cell proliferation.

The present invention moreover provides compositions when used for the treatment or prevention of a disease or condition, wherein said compositions comprise chaperonin 10 together with at least one pharmaceutically acceptable carrier, diluent or adjuvant, and wherein the chaperonin 10 modulates the level of cell surface expression of at least one MHC molecule.

The chaperonin 10 may further modulate the level of cell surface expression of at least one other cell surface molecule.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The present invention also provides compositions when used for the treatment or prevention of a disease or condition, wherein said compositions comprise chaperonin 10 together with at least one pharmaceutically acceptable carrier, diluent or adjuvant, and wherein the chaperonin 10 modulates the function of an antigen-presenting cell in a subject, or in at least one tissue or organ thereof.

The antigen-presenting cell may be selected from the group comprising a macrophage, dendritic cell or B cell.

The function may be selected from the group comprising migration to a lymph node, T cell activation or T cell proliferation.

The present invention additionally provides the use of chaperonin 10 for the manufacture of a medicament for the treatment or prevention of a disease or condition, wherein the chaperonin 10 modulates the level of cell surface expression of at least one MHC molecule.

The chaperonin 10 may further modulate the level of cell surface expression of at least one other cell surface molecule.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The present invention further provides the use of chaperonin 10 for the manufacture of a medicament for the treatment or prevention of a disease or condition, wherein the chaperonin 10 modulates the function of an antigen-presenting cell in a subject, or in at least one tissue or organ thereof.

The antigen-presenting cell may be selected from the group comprising a macrophage, dendritic cell or B cell.

The function may be selected from the group comprising migration to a lymph node, T cell activation or T cell proliferation.

The present invention moreover provides methods for modulating the production, localization within a cell and/or cell surface expression of one or more immunomodulators in a subject, or at least one cell, tissue or organ thereof, wherein said methods comprise administering an effective amount of chaperonin 10, and wherein the chaperonin 10 modulates the level of cell surface expression of at least one MHC molecule or at least one other cell surface molecule.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The present invention also provides processes for identifying a compound that modulates an immune response, wherein said processes comprise:

(a) contacting a cell or cell extract with a candidate compound in the presence of Cpn10; and (b) determining whether expression on the surface of said cell of at least one MHC molecule is modulated upon contact with said candidate compound.

The processes may further comprise:

(c) determining whether expression on the surface of said cell of at least one other cell surface molecule is modulated upon contact with said candidate compound.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The present invention additionally provides processes for screening a plurality of compounds to identify a compound that modulates an immune response, wherein said processes comprise:

(a) contacting a cell or cell extract with said plurality of compounds in the presence of Cpn10; and (b) determining whether expression on the surface of said cell of at least one MHC molecule is modulated upon contact with said plurality of compounds.

The processes may further comprise:

(c) determining whether expression on the surface of said cell of at least one other cell surface molecule is modulated upon contact with said plurality of compounds.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The present invention further provides processes for inducing modulation of the level of cell surface expression of at least one MHC molecule in a subject, or in at least one cell, tissue or organ thereof, wherein said processes comprise administering an effective amount of chaperonin 10.

The processes may further comprise modulation of the level of cell surface expression of at least one other cell surface molecule in a subject, or in at least one cell, tissue or organ thereof, comprising administering an effective amount of chaperonin 10.

The MHC molecule may be an MHC Class I molecule, an MHC Class II molecule, or a non-classical MHC molecule. The MHC Class II molecule may be HLA. The HLA may be HLA-DR, HLA-DP, or HLA-DQ.

The cell surface expression may be that of an antigen-presenting cell. The antigen-presenting cell may be selected from the group comprising a macrophage, dendritic cell or B cell.

The present invention moreover provides processes for identifying a compound that modulates an immune response, wherein said processes comprise:

(a) contacting a cell or cell extract with a candidate compound in the presence of Cpn10; and (b) determining whether the migration of said cell to a lymph node or the ability to activate and/or cause proliferation of T cells is modulated upon contact with said candidate compound.

The cell may be an antigen-presenting cell. The antigen-presenting cell may be selected from the group comprising a macrophage, dendritic cell or B cell.

The present invention also provides processes for screening a plurality of compounds to identify a compound that modulates an immune response, wherein said processes comprise:

(a) contacting a cell or cell extract with said plurality of compounds in the presence of Cpn10; and (b) determining whether the migration of said cell to a lymph node or the ability to activate and/or cause proliferation of T cells is modulated upon contact with said plurality of compounds.

The cell may be an antigen-presenting cell. The antigen-presenting cell may be selected from the group comprising a macrophage, dendritic cell or B cell.

The present invention additionally provides processes for modulating the function of an antigen-presenting cell in a subject, or in at least one tissue or organ thereof, wherein said processes comprise administering an effective amount of chaperonin 10.

The antigen-presenting cell may be selected from the group comprising a macrophage, dendritic cell or B cell.

The function may be selected from the group comprising migration to a lymph node, T cell activation or T cell proliferation.

Those skilled in the art will appreciate that in accordance with the methods of the present invention Cpn10 may be administered alone or in conjunction with one or more additional agents. For example, Cpn10 may be administered together with one or more TLR agonists capable of stimulating one or more of TLR3, TLR4, TLR7 and TLR9. Additionally, the present invention contemplates combination therapy using Cpn10 in conjunction with other therapeutic approaches to the treatment of diseases and disorders. For example, Cpn10 may be useful in the treatment of viral diseases which are responsive to therapy with Type I interferons such as IFNβ or IFNα. Further, as agonist-induced activation of TLR7 and TLR9 has previously been reported to enhance the response of tumours to radiation therapy, Cpn10 may be used in conjunction with radiation therapy for the treatment of cancer.

For such combination therapies, each component of the combination therapy may to be administered at the same time, or sequentially in any order, or at different times, so as to provide the desired effect. Alternatively, the components may be formulated together in a single dosage unit as a combination product. When administered separately, it may be preferred for the components to be administered by the same route of administration, although it is not necessary for this to be so.

Cpn10

In accordance with aspects and embodiments of the present invention, a subject in need of treatment is administered with an effective amount of Cpn10. In particular embodiments the subject to be treated is a human, and accordingly, the Cpn10 polypeptide is the human Cpn10 polypeptide. Those skilled in the art will appreciate that the precise identity of the Cpn10 used in accordance with the present invention may vary depending on a number of factors, for example the species to be treated, such that the Cpn10 may be selected so as to be derived from the species to be treated.

Cpn10 may be native, naturally-derived, recombinant or synthetic Cpn10. Methods described in Morton et al., 2000 (*Immunol Cell Biol* 78:603-607), Ryan et al., 1995 (*J Biol Chem* 270:22037-22043) and Johnson et al., 2005 (*J Biol Chem* 280:4037-4047) are examples of suitable production methods for recombinant and synthetic Cpn10 protein while methods described in Somodevilla-Torres et al., 2003 (*Protein Expression and Purification* 32:276-287), Ryan et al., 1995 (*J Biol Chem* 270:22037-22043) and Zhang et al., 2000 (*J Neurol Sci* 182:5-15) are examples of suitable production methods for native and naturally-derived Cpn10 protein although the skilled addressee will appreciate that the present invention is not limited by the method of purification or production used and any other method may be used to produce Cpn10 for use in accordance with the methods and compositions of the present invention.

Cpn10 polypeptides and peptide fragments for use in accordance with the present invention may be obtained using of standard recombinant nucleic acid techniques or may be synthesized, for example using conventional liquid or solid phase synthesis techniques. Cpn10 peptides may be produced by digestion of a polypeptide with one or more proteinases such as endoLys-C, endoArg-C, endoGlu-C and *staphylococcus* V8-protease. The digested peptide fragments can be purified by, for example, high performance liquid chromatographic (HPLC) techniques.

Embodiments of the invention also contemplate the administration of a polynucleotide encoding Cpn10. In such situations the polynucleotide is typically operably linked to a promoter such that the appropriate polypeptide sequence is produced following administration of the polynucleotide to the subject. The polynucleotide may be administered to subjects in a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences. The nucleic acid construct to be administered may comprise naked DNA or may be in the form of a composition, together with one or more pharmaceutically acceptable carriers.

The Cpn10 polypeptide may have the amino acid sequence as set forth in SEQ ID NO:1. The nucleotide sequence of the polynucleotide encoding Cpn10 may be as set forth in SEQ ID NO:4 or display sufficient sequence identity thereto to hybridise to the sequence of SEQ ID NO:4. In alternative embodiments, the nucleotide sequence of the polynucleotide may share at least 30%, 40%, 50%, 60%, 70%, 80%, 85%, 90%, 96%, 97%, 98% or 99% identity with the sequence set forth in SEQ ID NO:4.

Within the scope of the terms "polypeptide" and "polynucleotide" as used herein are fragments and variants thereof. By way of example only, peptide fragments of Cpn10 as described in WO 95/15338 (i.e. "Chaperonin 10" PCT application No. PCT/AU94/00740) may be used in accordance with aspects and embodiments of the present invention.

The term "fragment" refers to a nucleic acid or polypeptide sequence that encodes a constituent or is a constituent of full-length Cpn10 protein. In terms of the polypeptide the fragment possesses qualitative biological activity in common with the full-length protein. A biologically active fragment of Cpn10 used in accordance with the present invention may typically possess at least about 50% of the immunomodulatory activity of the corresponding full length protein, more typically at least about 60% of such activity, more typically at least about 70% of such activity, more typically at least about 80% of such activity, more typically at least about 90% of such activity, and more typically at least about 95% of such activity.

The term "variant" as used herein refers to substantially similar molecules. Generally, nucleic acid sequence variants encode polypeptides which possess qualitative biological activity in common. Generally, polypeptide sequence variants also possess qualitative biological activity in common. Further, these polypeptide sequence variants may share at least 50%, 55%, 60%, 65%, 70%, 75%, 80%, 85%, 90%, 95%, 96%, 97%, 98% or 99% sequence identity.

Further, a variant polypeptide may include analogues, wherein the term "analogue" means a polypeptide which is a derivative of Cpn10, which derivative comprises addition, deletion, substitution of one or more amino acids, such that the polypeptide retains substantially the same function as native Cpn10. It is well known in the art that some amino acids may be changed within a polypeptide without altering the activity of the polypeptide (conservative substitutions). The term "conservative amino acid substitution" refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution. Amino acid additions may result from the fusion of a Cpn10 polypeptide or fragment thereof with a second polypeptide or peptide, such as a polyhistidine tag, maltose binding protein fusion, glutathione S transferase fusion, green fluorescent protein fusion, or the addition of an epitope tag such as FLAG or c-myc. For example, the wild-type human Cpn10 polypeptide may comprise an additional GSM tripeptide moiety at the N-terminus (SEQ ID NO:2; see for example WO 95/15338, the disclosure of which is incorporated herein by reference) or an additional alanine (A) reside at the N-terminus (SEQ ID NO:3; WO 2004/041300 (i.e. "Chaperonin 10 immunosuppression" PCT application No. PCT/AU2003/001467)), the disclosure of which is incorporated herein by reference) or an additional glycine (G) residue at the N-terminus (SEQ ID NO:5; PCT/AU2006/001278 ("Modified Chaperonin 10" PCT application)), the disclosure of which is incorporated herein by reference. The present invention also contemplates the use of polynucleotides encoding such modified forms of Cpn10.

Cpn10 variants can be generated by mutagenesis of a Cpn10 protein or mutagenesis of an encoding nucleic acid, such as by random mutagenesis or site-directed mutagenesis using methods well known to those skilled in the art. Such methods may be found, for example in *Current Protocols In Molecular Biology* (Chapter 9), Ausubel et al., 1994, John Wiley & Sons, Inc., New York, the disclosure of which is incorporated herein by reference. Variants and analogues also encompass polypeptides complexed with other chemical moieties, fusion proteins or otherwise post-transitionally modified. Examples of suitable modifications are described in co-pending International Patent Application No. PCT/AU2005/000041, the disclosure of which is incorporated herein by reference.

Further, the Cpn10 polypeptide or fragment thereof may possess other post-translational modifications, including side-chain modifications such as for example acetylation, amidination, carbamoylation, reductive alkylation and other modifications as are known to those skilled in the art.

Compositions and Routes of Administration

In general, suitable compositions for use in accordance with the methods of the present invention may be prepared according to methods and procedures that are known to those of ordinary skill in the art and accordingly may include a pharmaceutically acceptable carrier, diluent and/or adjuvant.

Compositions may be administered by standard routes. In general, the compositions may be administered by the parenteral (e.g., intravenous, intraspinal, subcutaneous or intramuscular), oral or topical route. Administration may be systemic, regional or local. The particular route of administration to be used in any given circumstance will depend on a number of factors, including the nature of the condition to be treated, the severity and extent of the condition, the required dosage of the particular compound to be delivered and the potential side-effects of the compound.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The topical formulations of the present invention, comprise an active ingredient together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The compositions may be conjugated to an array of polyethylene glycol (PEG) derivatives. The addition of PEG to proteins (PEGylation) is a well established method for decreasing the plasma clearance rates of proteins, thereby increasing their efficacy (Nucci et al., 1991, *Adv. Drug Del. Rev.* 6:133). Additional benefits of PEGylation may include greater stability of proteins, decreased immunogenicity, enhanced solubility and decreased susceptibility to proteolysis (Sheffield W. 2001, *Curr Drug Targets Cardiovasc Haematol Disord.* 1:1-22). PEG molecules contain the basic repeating structure of —(OCH3CH2)n-OH and are classified into groups according to their molecular weight. PEG derivatives are conjugated to proteins to increase their hydrodynamic radius and in general, their increase in half-life is directly related to the size of the PEG chain attached (Sheffield W. 2001, *Curr Drug Targets Cardiovasc Haematol Disord.* 1:1-22).

The compositions may also be administered in the form of microparticles. Biodegradable microparticles formed from polylactide (PLA), polylactide-co-glycolide (PLGA), and epsilon-caprolactone (-caprolactone) have been extensively used as drug carriers to increase plasma half life and thereby prolong efficacy (R. Kumar, M., 2000, *J Pharm Pharmaceut Sci.* 3(2) 234-258). Microparticles have been formulated for the delivery of a range of drug candidates including vaccines, antibiotics, and DNA. Moreover, these formulations have been developed for various delivery routes including parenteral subcutaneous injection, intravenous injection and inhalation.

The compositions may incorporate a controlled release matrix that is composed of sucrose acetate isobutyrate (SAIB) and organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester, SAIB does not crystallize but exists as a clear viscous liquid. Mixing SAIB with a pharmaceutically accepted organic solvent such as ethanol or benzyl alcohol decreases the viscosity of the mixture sufficiently to allow for injection. An active pharmaceutical ingredient may be added to the SAIB delivery vehicle to form SAIB solution or suspension formulations. When the formulation is injected subcutaneously, the solvent diffuses from the matrix allowing the SAIB-drug or SAIB-drug polymer mixtures to set up as an in situ forming depot.

For the purposes of the present invention molecules and agents may be administered to subjects as compositions either therapeutically or preventively. In a therapeutic application, compositions are administered to a patient already suffering from a disease, in an amount sufficient to cure or at least partially arrest the disease and its complications. The composition should provide a quantity of the molecule or agent sufficient to effectively treat the patient.

The therapeutically effective dose level for any particular patient will depend upon a variety of factors including: the disorder being treated and the severity of the disorder; activity of the molecule or agent employed; the composition employed; the age, body weight, general health, sex and diet of the patient; the time of administration; the route of administration; the rate of sequestration of the molecule or agent; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m². Generally, an effective dosage is expected to be in the range of about 25 to about 500 mg/m², preferably about 25 to about 350 mg/m², more preferably about 25 to about 300 mg/m², still more preferably about 25 to about 250 mg/m², even more preferably about 50 to about 250 mg/m², and still even more preferably about 75 to about 150 mg/m².

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

Cpn10 Agonists and Antagonists

The present invention also contemplates the use of agonists and antagonists of Cpn10 and methods of screening and producing such agonists and antagonists.

Cpn10 agonists and antagonists may be specifically designed or screened according to their effect upon TLR3, TLR4, TLR7 and/or TLR9 signalling and immunomodulator secretion.

Antibodies may act as agonists or antagonists of Cpn10, or fragments or analogues thereof. Preferably suitable antibodies are prepared from discrete regions or fragments of the Cpn10 polypeptide, in particular those involved in conferring protease activity and/or partner or substrate binding. An antigenic Cpn10 polypeptide contains at least about 5, and preferably at least about 10, amino acids.

Methods for the generation of suitable antibodies will be readily appreciated by those skilled in the art. For example, an anti-Cpn10 monoclonal antibody, typically containing Fab portions, may be prepared using the hybridoma technology described in Antibodies—A Laboratory Manual, Harlow and Lane, eds., Cold Spring Harbor Laboratory, N.Y. (1988).

In essence, in the preparation of monoclonal antibodies directed toward Cpn10, or fragment or analogue thereof, any technique that provides for the production of antibody molecules by continuous cell lines in culture may be used. These include the hybridoma technique originally developed by Kohler et al., 1975, *Nature,* 256:495-497, as well as the trioma technique, the human B-cell hybridoma technique (Kozbor et al., 1983, *Immunology Today,* 4:72), and the EBV-hybridoma technique to produce human monoclonal antibodies (Cole et al., in *Monoclonal Antibodies and Cancer Therapy*, pp. 77-96, Alan R. Liss, Inc., (1985)). Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980).

In summary, a means of producing a hybridoma from which the monoclonal antibody is produced, a myeloma or other self-perpetuating cell line is fused with lymphocytes obtained from the spleen of a mammal hyperimmunised with a recognition factor-binding portion thereof, or recognition factor, or an origin-specific DNA-binding portion thereof. Hybridomas producing a monoclonal antibody useful in practicing this invention are identified by their ability to immunoreact with the present recognition factor and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Similarly, there are various procedures known in the art which may be used for the production of polyclonal antibodies. For the production of anti-Cpn10 polyclonal antibody, various host animals can be immunized by injection with Cpn10, or a fragment or analogue thereof, including but not limited to rabbits, chickens, mice, rats, sheep, goats, etc. Further, the Cpn10 polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary antibody. Alternatively, the antibody may be detected by virtue of its binding with a secondary antibody or reagent which is appropriately labelled. A variety of methods are known in the art for detecting binding in an immunoassay and are within the scope of the present invention.

The antibody (or fragment thereof) raised against Cpn10 or a fragment or analogue thereof has binding affinity for Cpn10. Preferably, the antibody (or fragment thereof) has binding affinity or avidity greater than about $10^5$ $M^{-1}$, more preferably greater than about $10^6$ $M^{-1}$, more preferably still greater than about $10^7 M^{-1}$ and most preferably greater than about $10^8 M^{-1}$.

In terms of obtaining a suitable amount of an antibody according to the present invention, one may manufacture the antibody(s) using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography may be used to remove residual proteins, solvents/detergents and nucleic acids. The purified antibody may be further purified and formulated into 0.9% saline using gel filtration columns. The formulated bulk preparation may then be sterilised and viral filtered and dispensed.

Agonists and antagonists other than antibodies are also contemplated. A candidate agonist or antagonist may be identified by an ability to form a molecular complex with TLR3, TLR4, TLR7 or TLR9, and optionally a TLR3, TLR4, TLR7 or TLR9 agonist. Further, a candidate antagonist may be identified by an ability to prevent or disrupt formation of a molecular complex comprising Cpn10, and TLR3, TLR4, TLR7 or TLR9, and optionally a TLR3, TLR4, TLR7 or TLR9 agonist.

Techniques and procedures for identifying and producing agonists and antagonists are well known to those skilled in the art, including screening of libraries of molecules such as synthetic chemical libraries such as combinatorial libraries, computer assisted screening of structural databases, computer-assisted modelling and/or design, or more traditional biophysical techniques which detect molecular binding interactions.

The present invention will now be further described in greater detail by reference to the following specific examples, which should not be construed as in any way limiting the scope of the invention.

EXAMPLES

Recombinant Human Cpn10

For the experiments described in the examples below, recombinant human Cpn10 (GenBank Accession No. X75821) was produced in *E. coli* as described in Johnson et al., 2005 (*J Biol Chem* 280:4037-4047). Purity was determined to be >97% by SDS-PAGE. Frozen aliquots of Cpn10 were thawed only once prior to use. All Cpn10 batches showed the same molar activity as *E. coli* GroES in GroEL-mediated rhodanese refolding assays (data not shown).

Example 1

General Materials and Methods

Cell Culture and Cell Signalling Molecules

Supplemented RPMI (SPP-036) containing 50 µM 2-mercaptoethanol (2-ME) (Gibco) and 1% non-essential amino acids (Gibco) was used in all cell culture experiments, together variously with recombinant human GM-CSF (R&D Systems, #215-GM, Lot No AR115021), recombinant human IL-4 (R&D Systems, #204 IL, Lot No AG235051), CD14+ Micro Beads (Miltenyi #130-050-201, Lot No 5050927008) and LPS from *E. coli* (Sigma #L6529, Lot No 015K4103).

Immature DC Generation

PBMC were prepared from healthy volunteers (LTP-062.02). PBMC stocks were stored in cryo-tubes in liquid nitrogen (LTP-063-03). Monocytes were purified by using CD14+ MicroBeads according to the manufacturer's instructions. $5 \times 10^7$ CD14+ monocytes were seeded into 75-cm$^2$ flasks in 20 ml supplemented RPMI containing 2-ME and non-essential amino acids. To generate immature DC, GM-CSF (10 µg/ml) plus IL-4 (10 µg/ml) (GM-CSF/IL-4-DC) was added to the cultures. On day 4 of culture, 10 ml of fresh medium containing cytokines was added.

DC Maturation in the Presence or Absence of Cpn10

Immature DC were harvested on day 5, washed and plated into 6-well plates at a concentration of $1 \times 10^6$ cells/well in 3 ml of supplemented RPMI/well. Maturation of DC was induced by LPS (0.12 ng/ml) for 20 hours. Cpn10 (10 µg/ml) was added 1 hour prior to the addition of LPS.

Cell-Surface Immunophenotyping

Mature DC were harvested, washed and labelled for 30 min at 4° C. using the following APC-Cy7-, PE- or APC-conjugated monoclonal antibodies (mAb) from BD: CD14-APC-Cy7, HLA-DR-APC, CD1a-PE, CD11c-PE, CD80-PE, CD83-PE, CD86-PE and CD40-PE. Isotypic controls used were $IgG_1$-APC-Cy7, -APC and -PE. Dead cells and debris were excluded from the analysis on the basis of their light scatter properties. The analysis was performed on a BD FACS-Array flow-cytometer.

Analysis of Cytokine Release by DC

DC were harvested on day 5 of culture, washed and plated into flat-bottomed microdilution plates at $1 \times 10^6$/ml. DC were matured with LPS (0.15 ng/ml) for 20 hours. To assess the effect of Cpn10 on DC cytokine production, Cpn10 (0.1-10 µg/ml) was added 1 hour prior to the addition of LPS. Supernatants were harvested and stored at −20° C. Accumulation of TNF-α in culture supernatants following incubation of DC with Cpn10 for 20 hours was assessed by ELISA using an R&D DuoSet Kit according to the manufacturer's instructions.

Primary Mixed Leukocyte Reaction (MLR) Assay

CD4+ T cells were purified from fresh blood by using a CD4 T cell Isolation Kit II (Miltenyi, #130-091-155, Lot No 5060928051) according to the manufacturer's instructions. Purity of T cells was routinely verified by flow cytometry. A total of $1 \times 10^5$ T cells were co-cultured with $1 \times 10^4$ DC in the presence or absence of Cpn10 (0.1-10 µg/ml) for 6 days. Supernatants were collected and analysed for IFN-γ accumulation by ELISA. Cell proliferation was assessed using a CyQUANT proliferation assay kit (Molecular Probes # C35006, Lot No 45179A) according to the manufacturer's instructions.

Example 2

Cpn10 Reduces DC Maturation In Vitro

Figure 1:
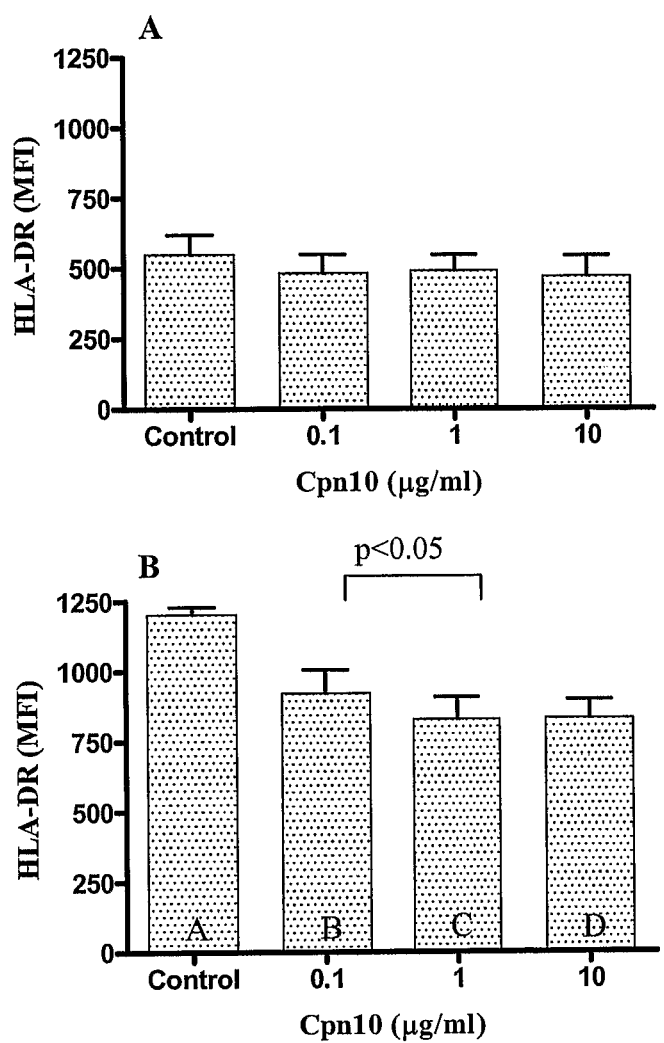
FIG. 1. Cpn10 significantly reduces HLA-DR expression on DC

Cultured monocyte-derived DC were used to assess the capacity of Cpn10 to modulate DC maturation in response to LPS. Conversion of monocytes into DC was verified by flow-cytometric analysis of CD1a and CD14 cell surface expression. CD1a+ CD14− DC were further analysed for surface expression of the maturation markers HLA-DR, CD40, CD80, CD83 and CD86. The mean fluorescence intensity (MFI) of HLA-DR in response to LPS (FIG. 1) was significantly reduced when Cpn10 was added during the maturation period (p<0.05). By contrast, the expression of HLA-DR was unchanged on immature DC incubated with Cpn10, in the absence of agonist. (FIG. 1 is representative of 3 independent experiments.)

In addition, it was found that when monocyte-derived DC were incubated together with Cpn10 for 20 hrs prior to testing of supernatant fluid, there was a significant and dose-dependent decrease in the constitutive release of TNF-α into the cell culture fluid. These results may reflect the ability of Cpn10 to reduce cell activation (FIG. 2, representative of 4 independent experiments).

Example 3

Cpn10 Modulation of T-Cell Stimulation by DC

The capacity of Cpn10 to modulate T cell stimulation by DC in a primary mixed-leukoocyte reaction (MLR) may be investigated together with analysis of the effect of Cpn10 on DC maturation in response to ligands such as prostaglandin $E_2$, IL-1β, IL-6 and TNF-α or soluble trimeric CD40L. As shown in FIG. 3, cultured monocyte-derived DC were used to assess the capacity of Cpn10 to modulate T cell activation in response to co-culture with allogeneic CD4$^+$ T cells for 6 days prior to testing of cell culture supernatant for IFN-γ production. Data shown in FIG. 3 (representative of two independent experiments) indicates IFN-γ accumulation was significantly reduced by Cpn10. Data shown in FIG. 4 demonstrate that Cpn10 does not affect T cell proliferation during a primary MLR, as determined by CyQUANT cell proliferation assay. (Data in FIG. 3 are representative of two independent experiments.)

Example 4

Compositions for Treatment

In accordance with the best mode of performing the invention provided herein, specific preferred compositions are outlined below. The following are to be construed as merely illustrative examples of compositions and not as a limitation of the scope of the present invention in any way.

Example 4(a)

Composition for Parenteral Administration

A composition for intramuscular injection could be prepared to contain 1 ml sterile buffered water, and 1 mg of a suitable compound.
Similarly, a composition for intravenous infusion may comprise 250 ml of sterile Ringer's solution, and 5 mg of a suitable compound.

Example 4(b)

Injectable Parenteral Composition

A composition suitable for administration by injection may be prepared by mixing 1% by weight of a suitable compound in 10% by volume propylene glycol and water. The solution is sterilised by filtration.

Example 4(c)

Capsule Composition

A composition of a suitable compound in the form of a capsule may be prepared by filling a standard two-piece hard gelatin capsule with 50 mg of the agent or compound, in powdered form, 100 mg of lactose, 35 mg of talc and 10 mg of magnesium stearate.

Example 4(d)

Eye Drop Composition

A typical composition for delivery as an eye drop is outlined below:

| | |
|---|---|
| Suitable compound | 0.3 g |
| Methyl Hydroxybenzoate | 0.005 g |
| Propyl Hydroxybenzoate | 0.06 g |
| Purified Water about to | 100.00 ml. |

The methyl and propyl hydroxybenzoates are dissolved in 70 ml purified water at 75° C., and the resulting solution is allowed to cool. The suitable compound is then added, and the solution sterilised by filtration through a membrane filter (0.22 μm pore size), and aseptically packed into sterile containers.

Example 4(e)

Composition for Inhalation Administration

For an aerosol container with a capacity of 20-30 ml: a mixture of 10 mg of a suitable compound with 0.5-0.8% by weight of a lubricating agent, such as polysorbate 85 or oleic acid, is dispersed in a propellant, such as freon, and put into an appropriate aerosol container for either intranasal or oral inhalation administration.

Example 4(f)

Ointment Composition

A typical composition for delivery as an ointment includes 1.0 g of a suitable compound, together with white soft paraffin to 100.0 g, dispersed to produce a smooth, homogeneous product.

---

The invention claimed is:

1. A method for treating a disease or condition selected from the group consisting of an autoimmune disorder, allergy, and asthma in a subject by modulating cell surface expression of at least one MHC molecule, wherein the method consists essentially of administering to the subject an effective amount of chaperonin 10, wherein the effective amount is about 0.01 mg to about 500 mg per kg body weight per 24 hours, thereby to treat the disease or condition selected from the group consisting of an autoimmune disorder, allergy, and asthma, wherein the chaperonin 10 is a human chaperonin 10 selected from the group consisting of SEQ ID NO: 1, SEQ ID NO: 2, and SEQ ID NO: 3.

2. The method according to claim 1, wherein the method further consists essentially of modulating cell surface expression of at least one costimulatory molecule.

3. A method for modulating cell surface expression of at least one MHC molecule in a subject having a disease or condition selected from the group consisting of an autoimmune disorder, allergy, asthma, or in at least one cell, tissue or organ thereof, wherein the method consists essentially of administering to the subject an effective amount of chaperonin 10, wherein the effective amount is about 0.01 mg to about 500 mg per kg body weight per 24 hours, such that the administration modulates cell surface expression of at least one MHC molecule in the subject to treat the disease or condition, wherein the chaperonin 10 is a human chaperonin 10 selected from the group consisting of SEQ ID NO: 1, SEQ ID NO: 2, and SEQ ID NO: 3.

4. The method according to claim 3, wherein the method further consists essentially of modulating cell surface expression of at least one costimulatory molecule in the subject, or in at least one cell, tissue or organ thereof.

5. The method according to claim 3, wherein the MHC molecule is selected from the group consisting of an MHC Class I molecule, an MHC Class II molecule, and a non-classical MHC molecule.

6. The method according to claim 5, wherein the MHC molecule is a MHC Class II molecule and the MHC Class II molecule is selected from the group consisting of HLA-DR, HLA-DP and HLA-DQ.

7. The method according to claim 3, wherein the cell surface expression is that of an antigen-presenting cell.

8. A method for modulating antigen-presenting cell function in a subject having a disease or condition selected from the group consisting of an autoimmune disorder, allergy, asthma, or in at least one tissue or organ thereof, wherein the method consists essentially of administering to the subject an effective amount of chaperonin 10, wherein the effective amount is about 0.01 mg to about 500 mg per kg body weight per 24 hours, such that the administration modulates antigen-presenting cell function in the subject or in at least one tissue or organ thereof to treat the disease or condition, wherein the chaperonin 10 is a human chaperonin 10 selected from the group consisting of SEQ ID NO: 1, SEQ ID NO: 2, and SEQ ID NO: 3.

9. The method according to claim 8, wherein the antigen-presenting cell is selected from the group consisting of a macrophage, a dendritic cell and a B cell.

10. The method according to claim 8, wherein the function is selected from the group consisting of migration to a lymph node, T cell activation and T cell proliferation.

11. A method for modulating production, localization within a cell and/or cell surface expression of one or more immunomodulators in a subject having a disease or condition selected from the group consisting of an autoimmune disorder, allergy, asthma, or at least one cell, tissue or organ thereof, wherein the method consists essentially of administering to the subject an effective amount of chaperonin 10, wherein the effective amount is about 0.01 mg to about 500 mg per kg body weight per 24 hours, and wherein the chaperonin 10 modulates cell surface expression of at least one MHC molecule to treat the disease or condition, wherein the chaperonin 10 is a human chaperonin 10 selected from the group consisting of SEQ ID NO: 1, SEQ ID NO: 2, and SEQ ID NO: 3.

12. The method according to claim 11, wherein the chaperonin 10 further modulates cell surface expression of at least one co-stimulatory molecule.

13. The method according to claim 11, wherein the MHC molecule is selected from the group consisting of an MHC Class I molecule, an MHC Class II molecule, and a non-classical MHC molecule.

14. The method according to claim 13 wherein the MHC molecule is a MHC Class II molecule and the MHC Class II molecule is selected from the group consisting of HLA-DR, HLA-DP and HLA-DQ.

15. The method according to claim 11, wherein the cell surface expression is that of an antigen-presenting cell selected from the group consisting of a macrophage, a dendritic cell and a B cell.

16. The method according to claim 1, wherein the MHC molecule is selected from the group consisting of an MHC Class I molecule, an MHC Class II molecule, and a non-classical MHC molecule.

17. The method according to claim 16, wherein the MHC molecule is a MHC Class II molecule and the MHC Class II molecule is selected from the group consisting of HLA-DR, HLA-DP and HLA-DQ.

18. The method according to claim 1, wherein the cell surface expression is that of an antigen-presenting cell.

19. The method according to claim 18, wherein the antigen-presenting cell is selected from the group consisting of a macrophage, a dendritic cell and a B cell.

20. The method according to claim 7, wherein the antigen-presenting cell is selected from the group consisting of a macrophage, a dendritic cell and a B cell.

* * * * *

SEQUENCE LISTING

```
<160> NUMBER OF SEQ ID NOS: 5

<210> SEQ ID NO 1
<211> LENGTH: 101
<212> TYPE: PRT
<213> ORGANISM: Homo sapiens

<400> SEQUENCE: 1

Ala Gly Gln Ala Phe Arg Lys Phe Leu Pro Leu Phe Asp Arg Val Leu
1               5                   10                  15
```

```
Val Glu Arg Ser Ala Ala Glu Thr Val Thr Lys Gly Ile Met Leu
         20                  25                  30

Pro Glu Lys Ser Gln Gly Lys Val Leu Gln Ala Thr Val Ala Val
         35                  40                  45

Gly Ser Gly Ser Lys Gly Lys Gly Gly Glu Ile Gln Pro Val Ser
 50                      55                  60

Lys Val Gly Asp Lys Val Leu Leu Pro Glu Tyr Gly Thr Lys Val
 65                  70                  75                  80

Val Leu Asp Asp Lys Asp Tyr Phe Leu Phe Arg Asp Gly Asp Ile Leu
                 85                  90                  95

Gly Lys Tyr Val Asp
            100

<210> SEQ ID NO 2
<211> LENGTH: 104
<212> TYPE: PRT
<213> ORGANISM: Homo sapiens

<400> SEQUENCE: 2

Gly Ser Met Ala Gly Gln Ala Phe Arg Lys Phe Leu Pro Leu Phe Asp
 1               5                  10                  15

Arg Val Leu Val Glu Arg Ser Ala Ala Glu Thr Val Thr Lys Gly Gly
                 20                  25                  30

Ile Met Leu Pro Glu Lys Ser Gln Gly Lys Val Leu Gln Ala Thr Val
                 35                  40                  45

Val Ala Val Gly Ser Gly Ser Lys Gly Lys Gly Gly Glu Ile Gln Pro
 50                      55                  60

Val Ser Val Lys Val Gly Asp Lys Val Leu Leu Pro Glu Tyr Gly Gly
 65                  70                  75                  80

Thr Lys Val Val Leu Asp Asp Lys Asp Tyr Phe Leu Phe Arg Asp Gly
                 85                  90                  95

Asp Ile Leu Gly Lys Tyr Val Asp
            100

<210> SEQ ID NO 3
<211> LENGTH: 102
<212> TYPE: PRT
<213> ORGANISM: Homo sapiens

<400> SEQUENCE: 3

Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Met
                 20                  25                  30

Leu Pro Glu Lys Ser Gln Gly Lys Val Leu Gln Ala Thr Val Val Ala
                 35                  40                  45

Val Gly Ser Gly Ser Lys Gly Lys Gly Gly Glu Ile Gln Pro Val Ser
 50                      55                  60

Val Lys Val Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Gly Asp Ile
                 85                  90                  95

Leu Gly Lys Tyr Val Asp
            100

<210> SEQ ID NO 4
```

```
<211> LENGTH: 309
<212> TYPE: DNA
<213> ORGANISM: Homo sapiens

<400> SEQUENCE: 4
atggcaggac aagcgtttag aaagtttctt ccactctttg accgagtatt ggttgaaagg      60
agtgctgctg aaactgtaac caaaggaggc attatgcttc cagaaaaatc tcaaggaaaa     120
gtattgcaag caacagtagt cgctgttgga tcgggttcta aaggaaaggg tggagagatt     180
caaccagtta gcgtgaaagt tggagataaa gttcttctcc cagaatatgg aggcaccaaa     240
gtagttctag atgacaagga ttatttccta tttagagatg gtgacattct tggaaagtac     300
gtagactga                                                             309

<210> SEQ ID NO 5
<211> LENGTH: 102
<212> TYPE: PRT
<213> ORGANISM: Homo sapiens

<400> SEQUENCE: 5

Gly Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```